United States Patent [19]

McGregor et al.

[11] Patent Number: 5,683,416

[45] Date of Patent: Nov. 4, 1997

[54] SURGICAL SUTURE NEEDLE OF THE TAPER POINT TYPE

[75] Inventors: Walter McGregor, Flemington, N.J.; William Schaeffer, Yardley, Pa.; Semyon Shchervinsky, Whitehouse Station, N.J.

[73] Assignee: Ethicon, Inc., Somerville, N.J.

[21] Appl. No.: 603,703

[22] Filed: Feb. 20, 1996

Related U.S. Application Data

[63] Continuation of Ser. No. 141,448, Oct. 22, 1993, abandoned.

[51] Int. Cl.⁶ .................................................. A61B 17/00
[52] U.S. Cl. ............................ 606/223; 606/222; 289/16; 223/102; 163/5
[58] Field of Search .............................. 606/222–227, 606/190; 112/222, 80.03; 289/16; 223/102–104; 163/5; 604/272–274

[56] References Cited

U.S. PATENT DOCUMENTS 4,237,892 12/1980 Ritter et al. ........................ 606/223
4,565,545 1/1986 Suzuki .............................. 604/272
4,901,722 2/1990 Noguchi ........................... 606/224
5,100,390 3/1992 Lubeck et al. ..................... 604/274

FOREIGN PATENT DOCUMENTS 0107961 5/1984 European Pat. Off. ............ 606/223
0174011 3/1986 European Pat. Off. ............ 604/272

*Primary Examiner*—Jeffrey A. Schmidt
*Attorney, Agent, or Firm*—Emil Richard Skula

[57] ABSTRACT

A taper point surgical needle having improved needle point strength is disclosed. In one embodiment of the needle, a tip portion includes first and second integral tapered regions having first and second cross-sectional areas respectively which decrease progressively toward the tip of the needle in accordance with first and second angles of inclination respectively, with the first angle being greater than the second angle. In another embodiment of the needle of the present invention, the tip portion includes a third tapered region integral with the second tapered region and having a cross-sectional area which decreases progressively toward the needle tip in accordance with a third angle of inclination which is smaller than the second angle.

11 Claims, 3 Drawing Sheets

SURGICAL SUTURE NEEDLE OF THE TAPER POINT TYPE

This is a continuation, of application Ser. No. 08/141,448, filed Oct. 22, 1993 now abandoned.

BACKGROUND OF THE INVENTION

1. Field of the Invention

This invention relates generally to surgical needles and, more particularly, to a taper point surgical needle having improved needle point strength by making the point from at least two tapered regions having different angles of inclination.

2. Description of the Prior Art

A surgical suture needle of the taper point type includes a proximal end portion defining a suture-mounting portion having a hole or channel to which a suture is to be attached, an intermediate portion defining a main body portion having a generally uniform cross-sectional area throughout an entire length thereof, and a distal end portion defining a tapered portion whose cross-sectional area decreases progressively toward a pointed distal end of the suture needle. The tapered portion has no cutting edges. The surgical needle may have the shape of some part of a circle which may be from a quarter of a circle to five-eighths of a circle.

In the design of surgical needles it is generally desirable for needles to exhibit favorable characteristics in two areas: strength and ease of penetration. It is desirable for a surgical needle to be strong enough to penetrate tissue which is being sutured without bending or breaking during a surgical procedure. It is also desirable for the needle to easily penetrate and smoothly pass through the tissue being sutured. The amount of force required for needle penetration of tissue includes that required for the engagement of the tip of the needle and for the widening of the hole. The suture needle of the taper point type is caused to pierce the tissue, forcibly opening the tissue without cutting the tissue. In other words, after the tip is engaged, a hole is made by pure blunt dilation with no cutting action whatsoever. Consequently, the suture needle of this type is used mainly for suturing blood vessels.

In conventional suture needles of the taper point type, the tapered portion is short, and its length is about 5 to 8 times the diameter of the main body. One of the reasons for this is that the resistance of the suture needle to the piercing through the blood vessel of the living body greatly depends on the degree of sharpness of the pointed end of the suture needle, and hardly depends on the amount (hereinafter referred to as "cross-sectional area increase rate") of increase of the cross-sectional area of the tapered portion per unit length from the pointed end toward the main body portion. Therefore, even if the tapered portion is made short, the piercing properties of the suture needle are not adversely affected. More specifically, the piercing resistance which the suture needle receives from the blood vessel of the living body is at the maximum level when piercing the skin of the blood vessel. This is due to the fact that the skin of the blood vessel has a greater rupture strength than the other parts of the blood vessel, and also due to the fact that the blood vessel of the living body has elasticity. The resistance of the suture needle to the piercing through the skin of the blood vessel greatly depends on the degree of sharpness of the point end of the suture needle. Once the suture needle pierces the skin of the blood vessel, the piercing resistance is abruptly reduced regardless of the value of the cross-sectional area increase rate of the tapered portion.

To provide a sharp taper point needle, U.S. Pat. No. 5,100,432 discloses a slender taper point needle whose tapered portion is in the range of between not less than 9 D and less than ⅔ L where D represents a diameter of a circle having the same cross-sectional area as that of the main body portion and L represents the overall length of the needle. However, the needle of U.S. Pat. No. 5,100,432 suffers from the problem that since the tapered portion is longer than conventional taper point needles, it has a more fragile tip with resultant bending over and burr formation which destroys the sharpness of the needle and decreases the strength of the needle tip portion.

The design techniques generally employed to meet the above two design criteria of strength and ease of penetration are often in conflict, however. One straightforward approach to improve the strength of a needle, for instance, is to increase its diameter, or thickness. But by increasing the thickness of the needle, the force necessary to penetrate the tissue is also increased, and the opening left in the tissue after passage of the needle is also enlarged. Likewise, penetration ease can be improved by making the needle thinner, but this approach as exemplified in U.S. Pat. No. 5,100,432 will correspondingly reduce the needle's strength. Thus, the design of a needle with favorable performance in both areas often requires that tradeoffs be made in the two criteria to arrive at a needle with optimal overall performance.

Thus, there is a need to develop a surgical needle of the taper point type which has improved needle point strength and is strong enough to retain its structural integrity, resist bending and burr formation.

SUMMARY OF THE INVENTION

The present invention is directed to a surgical needle of the taper point type which has improved needle body strength while retaining ease of penetration. The taper point needle of the present invention includes a tip portion which terminates in a pointed tip. Moreover, the tip portion has two or more integral tapered regions whose cross-sectional areas decrease at different rates toward a distal end of the tip portion. The provision of the two or more tapered regions improves upon prior art taper point needles in that the needles of the present invention are less likely to bend or deform when used to penetrate the blood vessel of a patient.

In one embodiment of the needle of the present invention, the tip portion includes first and second integral tapered regions whose cross-sectional area decreases toward a distal end of the tip portion which is pointed. The first tapered region has a first angle of inclination greater than 4°. The second tapered region has a second angle of inclination less than 5°. The two integral tapered regions blend smoothly with each other at a transition region where they meet such that there are no sharp edges or discontinuities at the transition region.

In another embodiment of the present invention, the tip portion of the needle further includes a third tapered region which is integral with the second tapered region and has a cross-sectional area which decreases progressively toward the pointed tip of the needle. The third tapered region has a third angle of inclination less than 5°. The outer surface of a transition region between the second and third tapered regions has a smooth surface such that there are no sharp edges at the transition region.

For each of the above described embodiments, the length of the first tapered region along the axis of the needle is less than 9 D. By providing a taper point needle with at least two tapered regions having different angles of inclination, the needles of the present invention are a significant improvement over conventional taper point needles. The improved taper point needles of the present invention provide a sharp point with increased needle point strength which is resistant to bending or deformation.

DETAILED DESCRIPTION OF THE INVENTION

Figure 1:
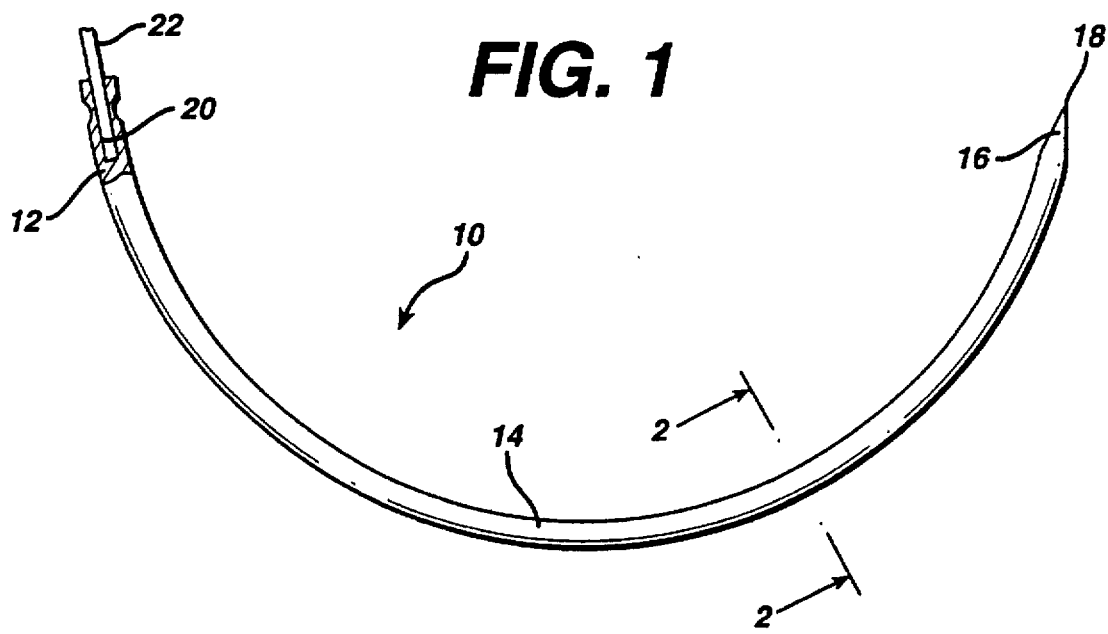
FIG. 1 is a perspective view of one embodiment of a taper point type suture needle of the present invention.

Referring to FIG. 1, there is shown one embodiment of the taper point surgical needle 10 of the present invention. The needle 10 includes a suture mounting portion 12, a contiguous main body portion 14 having a generally uniform cross-sectional area throughout an entire length thereof an a contiguous tip portion 16.

The suture mounting portion 12 is straight and has a hole 20 extending from a proximal end face of the suture needle along an axis thereof. The length of the suture mounting portion 12 is generally equal to or slightly greater than the length of the hole 20. A suture 22 is inserted at one end portion into hole 20 and then the suture mounting portion 12 is deformed or compressed to hold the suture 22.

Figure 2:
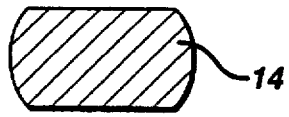
FIG. 2 is a cross-sectional view taken along the line 2—2 of FIG. 1.
Figure 3:
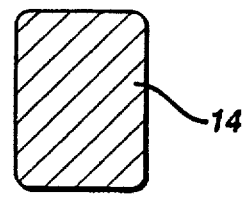
FIG. 3 is an alternative embodiment of the cross-sectional view taken along lines 2—2 in FIG. 1.

The cross-sectional shape of the main body portion 14 can have a wide variety of conventional shapes including circular, square and rectangular. However, in order to provide stability and control of needle 10 during use, the main body portion 14 can have a flat pressed circular cross section such as shown in FIG. 2 or, alternatively, a modified square cross-sectional shape as shown in FIG. 3. In the needle 10, the main body portion 14 and the tip portion 16 are curved and can possess a constant radius of curvature. This configuration is, however, not critical to the present invention and body portion 14 and tip portion 16 can therefore assume any straight and/or curved configuration which is considered suitable for the particular purpose that is intended.

The needle 10 is rigidly formed of a suitable material for suture needle use inside the body such as surgical grade steel, moretnsite-type stainless steel and precipitation hardened stainless steel.

Figure 4:
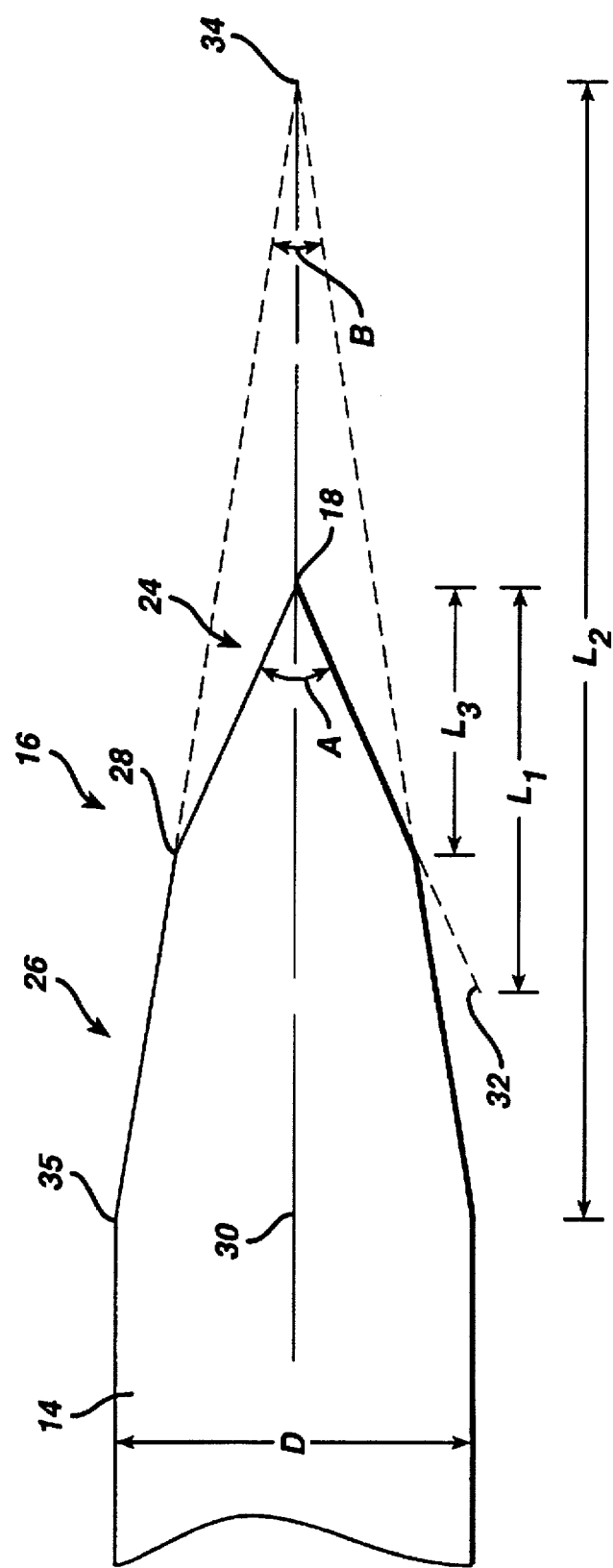
FIG. 4 is an englarged side elevational view of the distal end portion of the suture needle of FIG. 1 prior to being curved.

Referring to FIG. 4, there is shown one embodiment of a tip portion of the surgical needle of the present invention. The tip portion 16 of the needle includes a first tapered region 24 and an integral second tapered region 26. The first tapered region 24 has a circular cross-section which decreases progressively from its proximal end 28 to the distal end 18. The first tapered region 24 terminates in a pointed tip 18 which is configured to permit piercing of blood vessels of the body. The second tapered region 26 has a circular cross-section which decreases progressively from its proximal end 35 to its distal end 28. The tip portion undergoes a transition from the first tapered region 24 to the second tapered region 26 at transition region 28 such that there are no sharp edges at region 28. This can be done by blending the region 28 between the two adjacent tapered regions.

The angle of inclination of each tapered region can be defined by a length extending from the apex of each region extended to a point where the region would equal the diameter of the main body portion. For example, the length $L_1$ along the axis 30 of the needle is defined as the length from tip 18 to a point 32 at which the cross-sectional diameter would be equal to the diameter D. Similarly, length $L_2$ along the axis 30 of needle 10 is defined as the distance between a tip 34 if the walls of the second region 26 were extended to the point 34, and the proximal end 35 where the second region has the diameter D equal to that of the main body portion.

In order to provide improved needle body strength over a conventional taper point needle, the first tapered region 24 is at an angle of inclination A greater than 4°, while the second tapered region 26 is at an angle of inclination B less than 5°. In addition, the length $L_3$ from tip 18 to the distal end 28 along the axis 30 is less than 9 D. By forming the needle 10 with two tapered regions with different angles, the strength of the needle tip is greatly increased while the force needed to penetrate a blood vessel is retained.

Figure 5:
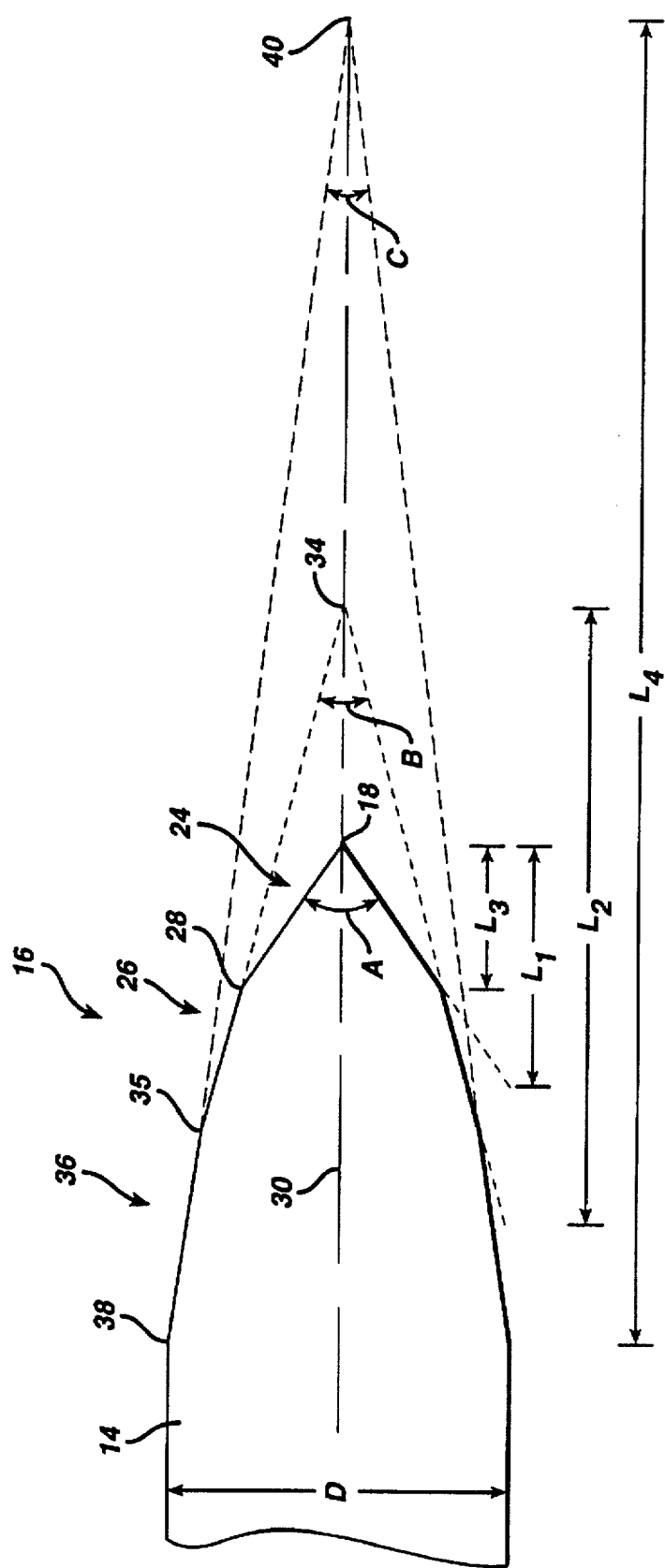
FIG. 5 is an enlarged side elevational view of the distal end portion of another embodiment of the suture needle of the present invention prior to being curved.

Referring to FIG. 5, there is shown another embodiment of a tip portion of a surgical needle of the present invention. In this embodiment, the needle tip portion 16 includes three tapered regions. The first and second tapered regions 24 and 26 are described above with regard to FIG. 4 and thus not repeated herein. A third tapered region 36 has a circular cross-sectional shape which decreases progressively from its proximal end 38 to its distal end 35. The needle 10 at proximal end 38 is at its full diameter D. The tip portion undergoes a transition from the second tapered region 26 to the third tapered region 36 at transition region 35 such that there are no sharp edges at region 35. This is done by blending the surface at region 35 between the two adjacent tapered regions. In a similar fashion to defining $L_1$ and $L_2$, the length $L_4$ along the axis 30 of the needle is defined as the length from a point 40 which corresponds to extending the walls of the third tapered region 36 to a point where they meet, and the proximal end 38 where the third tapered region 36 has a diameter D equal to that of the main body portion 14. The third tapered region 36 is at an angle C less than 5°.

It should be understood that although the needle of the present invention has been described as having two or three integral tapered regions, the needle can be formed with more than three tapered regions.

While the invention has been particularly shown and described with respect to illustrative and preferred embodiments thereof, it will be understood by those skilled in the art that the foregoing and other changes in form and details may be made therein without departing from the spirit and scope of the invention which should be limited only to the scope of the appended claims.

What is claimed is:

1. A surgical needle of a taper point type comprising:
   a taper point surgical needle having a length and a circular cross-section along its length and having a tip portion, said tip portion having first and second tapered regions whose cross-sectional area decreases toward a distal end of a tip portion which is pointed, the first tapered region having a first angle of inclination greater than or equal to 6° and said second tapered region having a second angle of inclination less than or equal to 5°, wherein said cross-section of said first and second tapered regions is circular.

2. The surgical needle according to claim 1, wherein said diameter is between about 0.001" to 1.000".

3. The surgical needle according to claim 1, further including a suture mounting portion having a hole to which a suture is to be attached and a body portion which is disposed between and integral with the suture mounting portion and the tip portion.

4. The surgical needle according to claim 3, wherein said body portion has a generally uniform circular cross-sectional area throughout an entire length thereof.

5. The surgical needle according to claim 4, wherein said needle has an overall curved shape with a constant radius of curvature.

6. The surgical needle according to claim 1, wherein said tip portion further includes a third tapered region integral with said second tapered region and having a cross-sectional area which decreases progressively toward the distal end of the needle, said third tapered region having a third angle of inclination equal to 5°.

7. The surgical needle according to claim 6, wherein said cross-section of said first, second and third tapered regions is circular.

8. The surgical needle according to claim 7, wherein said diameter is between about 0.0001" to 1.000".

9. The surgical needle according to claim 7, further including a suture mounting portion having a hole to which a suture is to be attached and a body portion which is disposed between and integral with the suture mounting portion and the tip portion.

10. The surgical needle according to claim 9, wherein said body portion has a generally uniform circular cross-sectional area throughout an entire length thereof.

11. The surgical needle according to claim 10, wherein said needle has an overall curved shape with a constant radius of curvature.

* * * * *